United States Patent
Huang et al.

(10) Patent No.: US 10,238,768 B2
(45) Date of Patent: Mar. 26, 2019

(54) WOUND-HEALING AND HEMOSTATIC SPONGE OF SQUID INK POLYSACCHARIDE/CHITOSAN, PREPARATION METHOD AND USE THEREOF

(71) Applicant: Guangdong Ocean University, Zhanjiang (CN)

(72) Inventors: Na Huang, Zhanjiang (CN); Sidong Li, Zhanjiang (CN); Zhang Hu, Zhanjiang (CN); Chengpeng Li, Zhanjiang (CN); Songzhi Kong, Zhanjiang (CN); Yu Cheng, Zhanjiang (CN); Pengzhi Hong, Zhanjiang (CN); Rongqiong Luo, Zhanjiang (CN); Qianqian Ouyang, Zhanjiang (CN); Gaorong Li, Zhanjiang (CN)

(73) Assignee: Guangdong Ocean University, Zhanjiang (CN)

( * ) Notice: Subject to any disclaimer, the term of this patent is extended or adjusted under 35 U.S.C. 154(b) by 25 days.

(21) Appl. No.: 15/704,673

(22) Filed: Sep. 14, 2017

(65) Prior Publication Data
US 2018/0117212 A1 May 3, 2018

(30) Foreign Application Priority Data
Oct. 28, 2016 (CN) ............. 2016 1 0966793

(51) Int. Cl.
| | |
|---|---|
| *C08K 3/16* | (2006.01) |
| *C08L 5/00* | (2006.01) |
| *C08L 5/08* | (2006.01) |
| *F26B 5/06* | (2006.01) |
| *A61L 24/00* | (2006.01) |
| *A61L 24/02* | (2006.01) |
| *A61L 24/04* | (2006.01) |
| *A61L 24/08* | (2006.01) |
| *C08B 37/08* | (2006.01) |

(52) U.S. Cl.
CPC ........... *A61L 24/08* (2013.01); *A61L 24/0005* (2013.01); *A61L 24/0036* (2013.01); *A61L 24/02* (2013.01); *A61L 24/043* (2013.01); *C08B 37/003* (2013.01); *C08L 5/08* (2013.01); *F26B 5/06* (2013.01); *A61L 2400/04* (2013.01); *C08K 2003/162* (2013.01)

(58) Field of Classification Search
CPC .. C08L 5/08; C08L 5/00; A61L 24/043; A61L 2400/04; A61L 24/0005; A61L 24/0036; A61L 24/02; A61L 24/08; C08B 37/003; C08K 2003/162; F26B 5/06
See application file for complete search history.

(56) References Cited

FOREIGN PATENT DOCUMENTS

| | | | |
|---|---|---|---|
| CN | 102526795 A | * | 7/2012 |
| CN | 105327383 | | 2/2016 |

OTHER PUBLICATIONS

Luo et al (African Journal of Pharmacy and Pharmacology, 2013, vol. 7, pp. 1382-1388).*
English translation of CN 102526795 A, Espacenet, downloaded Apr. 2018.*
Englehart, Michael S. MD et al. "A Novel Highly Porous Silica and Chitosan-Based Hemostatic Dressing is Superior to HemCon and Gauze Sponges." Journal of Trauma-Injury Infection & Critical Care: Oct. 2008—vol. 65—Issue 4—pp. 884-892.
Ersoy G et al. "Hemostatic effects of microporous polysaccharide hemosphere in a rat model with severe femoral artery bleeding." Advances in Therapy, May/Jun. 2007, vol. 24, No. 3, pp. 485-492.
Gu, R. et al. "The performance of a fly-larva shell-derived chitosan sponge as an absorbable surgical hemostatic agent." Biomaterials, 31 (6), Feb. 1, 2010; pp. 1270-1277.
He, Qing et al. "Positive charge of chitosan retards blood coagulation on chitosan films." Journal of Biomaterials Applications, vol. 27 issue: 8, May 1, 2013, pp. 1032-1045.
Kilkenny, C. et al. "Improving bioscience research reporting: the ARRIVE guidelines for reporting animal research." PLoS Biology, vol. 8, Issue 6, Jun. 2010, 5 pages.
Le, XY et al. "Interventional effects of squid ink polysaccharides on cyclophosphamide-associated testicular damage in mice." Bratislavske Lekarske Listy, 116, 5, 2015 pp. 334-339.
Pozza, Morenoa et al. "Celox (chitosan) for haemostasis in massive traumatic bleeding: experience in Afghanistan." European Journal of Emergency Medicine: Feb. 2011—vol. 18—Issue 1—p. 31-33.

* cited by examiner

*Primary Examiner* — Mark V Stevens
(74) *Attorney, Agent, or Firm* — JCIPRNET

(57) ABSTRACT

A wound-healing and hemostatic sponge of squid ink polysaccharide/chitosan, a preparation method and use thereof are provided. The sponge comprises squid ink polysaccharide and chitosan as carriers and calcium chloride as an initiator for blood coagulation, and the wound-healing and hemostatic sponge of squid ink polysaccharide/chitosan is achieved via a lyophilization technology. Particularly, the preparation method comprises slowly adding a squid ink polysaccharide solution to a chitosan solution to form a uniformly mixed solution, adding a calcium chloride solution to the uniformly mixed solution, forming a gel followed by the gel being frozen and then lyophilized, and achieving the product. The wound-healing and hemostatic sponge has a good absorbing-errhysis effect, a good pro-coagulant effect, fast hemostasis and a complete hemostatic effect, without secondary re-hemorrhage. Moreover, the wound-healing and hemostatic sponge can promote wound healing, re-epithelialization and repair of epidermis and dermis, with strong wound-healing ability, good biocompatibility, weak toxic side effects and irritation, belonging to a novel wound-healing and hemostatic material. Moreover, the preparation method is reliable, fast, and low cost.

18 Claims, 4 Drawing Sheets
(4 of 4 Drawing Sheet(s) Filed in Color)

WOUND-HEALING AND HEMOSTATIC SPONGE OF SQUID INK POLYSACCHARIDE/CHITOSAN, PREPARATION METHOD AND USE THEREOF

CROSS-REFERENCE TO RELATED APPLICATION

This application claims the benefit of priority to Chinese Application No. 201610966793.1 filed on Oct. 28, 2016, the content of which is incorporated herein by reference in its entirety for all purposes.

TECHNICAL FIELD

The present invention relates to a technical field of wound-healing materials, and specifically relates to a wound-healing and hemostatic sponge of squid ink polysaccharide/chitosan, a preparation method and use thereof.

BACKGROUND

Uncontrollable massive hemorrhage is a primary cause of death during wars, traffic accidents, and other accidents. Safe and efficient hemostatic and healing materials can effectively decrease mortality caused by the hemorrhage. As a novel wound-healing and hemostatic material, the wound-healing and hemostatic material is considered as one of the most effective materials for hemostasis of a topical trauma, with advantages such as being absorbable, efficient, economical and non-toxic. As the requirement for the hemostasis of the topical trauma during a treatment becomes higher and higher, a hemostatic effect of the wound-healing and hemostatic material seems more and more important. The wound-healing and hemostatic material reaches the hemostatic effect and realizes wound healing mainly by the characteristics and advantages itself, i.e. adsorbing blood, aggregating blood platelets, occluding blood vessels, promoting generation of thrombin or activating blood coagulation factors, promoting a series of process that proliferation and migration of repair cells as well as tissue reconstruction. However, at present, a high-end sterilized absorbable hemostatic material and a medical material which can promote the wound healing are restricted using due to their high cost.

Additionally, large amounts of high molecular materials are generated during marine product processing, and their utilization is simple with low additional value, limiting marine economic development. As a high molecular material generated during the processing of marine products, chitosan has good biocompatibility and antibacterial activity, and is also low cost. A pro-coagulant activity of chitosan was first reported by Malette et al. Chitosan is a natural polymer from deacetylated chitin, with extensive sources and good biocompatibility. Chitosan generally makes erythrocytes aggregate and thus leading to blood coagulation. In the prior art, biomaterials commonly used in clinic such as chitosan sponge, absorbable gelatin sponge and the like have different characteristics in hemostasis mechanisms and effects on promoting the wound healing, due to their different components. At present, a few hemostatic agents of which a main component is chitosan have come into market, such as Celox hemostatic agent (Pozza M et al. EUR J EMERG MED. 2011) and HemCon hemostatic bandage (Englehart M S et al. J Trauma. 2008), mainly used in emergency hemostasis for war wound and civil accidents. However, it has been reported that the hemostatic effect of the chitosan material is limited when dealing with severe injuries, which may be relative to excessive positive charges of chitosan that inhibit the blood coagulation. Moreover, it has been found in a hemostasis experiment on a rat liver with a chitosan acetate sponge that when the chitosan acetate sponge contacted with blood, partial substrate of the sponge would be dissolved and a pore structure of the sponge would collapse due to an electrostatic repulsive interaction between the chitosan molecules with positive charges, so that the sponge thus could not fit into a wound surface tightly and to some extent the hemostatic effect of the chitosan acetate sponge would be reduced (He Q et al. J BIOMATER APPL 2013). Additionally, CN201510573494.7 discloses a composite hemostatic sponge of collagen/calcium alginate/chitosan. Although it has solved problems of the hemostatic sponge in biocompatibility, hygroscopicity and initiators for blood coagulation, a problem of incomplete hemostasis still exists. Therefore, the hemostatic effect of the healing material which is based on chitosan needs to be further improved.

Squid ink has exhibited efficacy for the treatment of cardiodynia caused by hemorrhage which was recorded in a medical book of ancient China, Compendium of Materia Medica. It has been proved in the modern clinical application that the squid ink, as a systemically hemostatic drug, has a remarkable hemostatic effect on various hemorrhagic symptoms including gynecology, surgery and internal medicine, without toxicity and side effects. However, hemostatic application of the squid ink is still insufficient at present.

SUMMARY OF THE INVENTION

The technical problem to be solved by the present invention is to overcome an insufficiency of wound-healing and hemostatic material in the prior art and deficiencies of a hemostatic agent based on chitosan (CS), such as unsatisfactory effect, poor biocompatibility, long hemostatic time, incomplete hemostasis, poor effect on absorbing errhysis, weak wound-healing ability, toxic side effects, strong irritation and long preparation time, to combine squid ink polysaccharide (SIP) into a macromolecular chitosan sponge, and to develop a wound-healing and hemostatic sponge of squid ink polysaccharide/chitosan which can stop bleeding rapidly and promote healing of skin.

An object of the present invention is to provide a preparation method for the wound-healing and hemostatic sponge of squid ink polysaccharide/chitosan.

The second object of the present invention is to provide the prepared wound-healing and hemostatic sponge of squid ink polysaccharide/chitosan (denoted as SIP-CS).

The third object of the present invention is to provide use of the wound-healing and hemostatic sponge of squid ink polysaccharide/chitosan in hemostasis and/or wound healing.

The objectives of the present invention are realized by the following technical solutions:

A preparation method for the wound-healing and hemostatic sponge of squid ink polysaccharide/chitosan which comprises two marine biomaterials, squid ink polysaccharide and chitosan, as carriers and calcium chloride as an initiator for blood coagulation, achieves the wound-healing and hemostatic sponge of squid ink polysaccharide/chitosan via a lyophilization technology.

In the present invention, the SIP is combined into the macromolecular chitosan to cover a negative effect of positive charges of chitosan so that cooperation of these two may promote a coagulation process coordinately. Also, an optimal formulation for preparing the wound-healing and hemostatic sponge is optimized by a central composite design-response surface methodology. In order to evaluate an application effect of this novel material, animal hemorrhage models and an animal scalded model are established to carry out the experiments. In the experiments of rabbit ear artery, liver and femoral artery hemorrhage models, compared with conventional hemostatic materials such as chitosan dressing and absorbable gelatin, the SIP-CS takes less time to stop the hemorrhage resulting in less bleeding. It can be observed by a scanning electron microscope that the SIP-CS may adsorb large amounts of blood cells to achieve an effect of fast hemostasis. In an aspect of wound healing, by observing a healing area and a pathological section of scalded wound of New Zealand rabbit, it is found that the SIP-CS group can promote the wound healing faster than the chitosan group, and even exhibits a better effect than a commercial moist exposed burn ointment. The SIP-CS is an excellent wound-healing and hemostatic material that can stop bleeding rapidly, promote burnt or scalded skin healing and prevent a wound infection.

Particularly, the preparation method for the wound-healing and hemostatic sponge of squid ink polysaccharide/chitosan of the present invention is as follows: slowly adding a squid ink polysaccharide solution to a chitosan solution, to form a uniformly mixed solution, adding a calcium chloride solution to the uniformly mixed solution, forming a gel follow by the gel being frozen and then lyophilized, and achieving the product.

Particularly, preferably the squid ink polysaccharide solution has a concentration of 0.4 to 0.8 mg/mL.

More preferably, the squid ink polysaccharide solution has the concentration of 0.55 mg/mL.

Preferably, the chitosan solution has a mass concentration of 1.5 to 3.5%.

More preferably, the chitosan solution has the mass concentration of 2.29%.

Preferably, the calcium chloride solution has a mass concentration of 2 to 6%.

More preferably, the calcium chloride solution has the mass concentration of 2.82%.

Preferably, a volume ratio of the squid ink polysaccharide solution, the chitosan solution and the calcium chloride solution is 4-6:13-17:1-3.

More preferably, the volume ratio of the squid ink polysaccharide solution, the chitosan solution and the calcium chloride solution is 5:15:2.

Preferably, a condition of freeze is frozen at −30° C. to −10° C. for 10 to 15 hours.

More preferably, the condition of freeze is frozen at −20° C. for 12 hours.

Preferably, duration for the lyophilization is 16 to 20 hours.

More preferably, the duration for the lyophilization is 16 hours.

Above preparation process of the present invention is optimized by the central composite design-response surface methodology, i.e. chitosan, squid ink polysaccharide and calcium chloride concentrations as investigation factors, a comprehensive score of appearance quality and a water absorption capacity of the sponge product as investigation indices, an experiment result table of the central composite design is generated via Design-Expert.V8.0.6 software. A response surface figure is generated by the variance analysis of the experiment result, and thus the optimal formulation is achieved after analyzing the response surface figure. The optimal formulation is as follows: the chitosan concentration of 2.29%, the squid ink polysaccharide concentration of 0.55 mg/ml and the calcium chloride concentration of 2.82%. The sponge product is prepared according to the optimal formulation achieved via the software and is compared with a predicted index value, and finally the prepared wound-healing and hemostatic sponge of squid ink polysaccharide/chitosan has good quality.

Thus, as the optimal implementation, the preparation method for the wound-healing and hemostatic sponge of squid ink polysaccharide/chitosan of the present invention is as follows: slowly adding the squid ink polysaccharide solution in a concentration of 0.55 mg/ml to the chitosan solution in a mass concentration of 2.29%, to form a uniformly mixed solution, adding 2 mL of the calcium chloride solution in a mass concentration of 2.82% to the uniformly mixed solution, forming a gel follow by the gel being frozen at −20° C. for 12 hours and then being lyophilized for 16 hours, and achieving the product. The volume ratio of the squid ink polysaccharide solution, the chitosan solution and the calcium chloride solution is 5:15:2.

Additionally, the slowly adding is carried out with stirring. The uniformly mixed solution is also carried out with stirring.

A solvent of the squid ink polysaccharide solution is purified water.

A solvent of the chitosan solution is 1% acetic acid solution.

Additionally, the wound-healing and hemostatic sponge of squid ink polysaccharide/chitosan (SIP-CS) prepared by the above method is also within the protection scope of the present invention.

The SIP-CS of the present invention has very good hemostatic and wound-healing effect, and thus use of the SIP-CS in hemostasis and/or wound healing as well as use thereof in preparing hemostatic material and/or wound-healing material are within the protection scope of the present invention.

Particularly, the wound comprises scalded wound, burnt wound and the like. The wound healing specifically refers to promoting wound union, re-epithelialization and repair of epidermis and dermis, and thus realizing the wound healing.

Specifically, a method of using the SIP-CS of the present invention comprises applying the SIP-CS onto the wound, compressing the wound to stop bleeding and the fast hemostasis may be realized; dressing the wound, replacing the sponge regularly and the wound-healing effect may be performed continuously.

Compared with the prior art, the present invention has following beneficial effects:

In the present invention, two marine biomaterials, squid ink polysaccharide and chitosan, as carriers and calcium chloride as the initiator for blood coagulation, a core material with excellent performance, i.e. a squid ink polysaccharide-chitosan composite sponge (SIP-CS) is achieved via the lyophilization technology, as a novel wound-healing material. Optimal preparation process conditions are optimized by using the central composite design-response surface methodology (CCD method), the comprehensive score of appearance quality and the water absorption capacity of the composite sponge as evaluation indices. A performance evaluation result of the squid ink polysaccharide-chitosan sponge (SIP-CS) shows that the SIP-CS can adsorb large amounts of blood cells and stop bleeding rapidly, and no secondary re-hemorrhage occurs; moreover the SIP-CS can promote wound union, re-epithelialization and repair of epidermis and dermis. Therefore, the SIP-CS is a novel marine biomaterial for hemostasis and promoting wound healing with a very good application prospect and provides a research basis to research of novel hemostatic agent.

In the solution of the present invention, chitosan, as a medical material, performs hemostasis and in the meantime allows a mixed solution to form a hydrogel due to its viscosity, leading to a fine appearance as well as good adsorbability of the sponge product, and properties of blocking the wound and adsorbing errhysis are greatly improved when the sponge product performs hemostasis. A main function of squid ink polysaccharide is to provide a strong and complete hemostatic effect which can shorten a blood coagulation time and a bleeding time with a pro-coagulant effect, to cover a shortage of that chitosan is not able to activate a blood coagulation factor XII. Thereby a multi-channel hemostatic mechanism is created which significantly improves the hemostatic property of the material.

Simultaneously, the wound-healing and hemostatic sponge of squid ink polysaccharide/chitosan (SIP-CS) prepared in the present invention is conducive to sticking to the wound, characterized by a spongy property, strong water-absorbability and tackiness. Squid ink polysaccharide (SIP) and chitosan (CS) as conventionally abandoned marine resources, are low-cost raw materials of which are taken full advantage.

Additionally, the preparation process for the wound-healing and hemostatic sponge in the present invention is reliable, takes less time than most of the similar research and less energy consumption, and improves a production efficiency. The prepared wound-healing and hemostatic sponge has good biocompatibility, short hemostatic time, good absorbing-errhysis effect, complete hemostasis, strong wound-healing ability, weak toxic side effects and irritation, and extensive application value.

BRIEF DESCRIPTION OF THE DRAWINGS

The patent application file contains at least one drawing executed in color. Copies of this patent application with color drawing(s) will be provided by the Office upon request and payment of the necessary fee.

Figure 1:
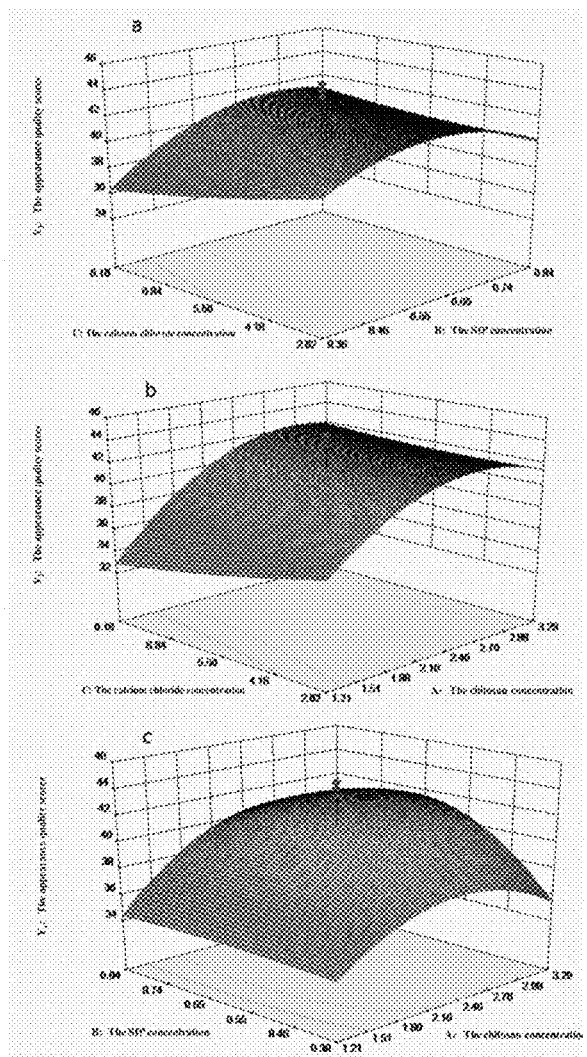
Figure 2:
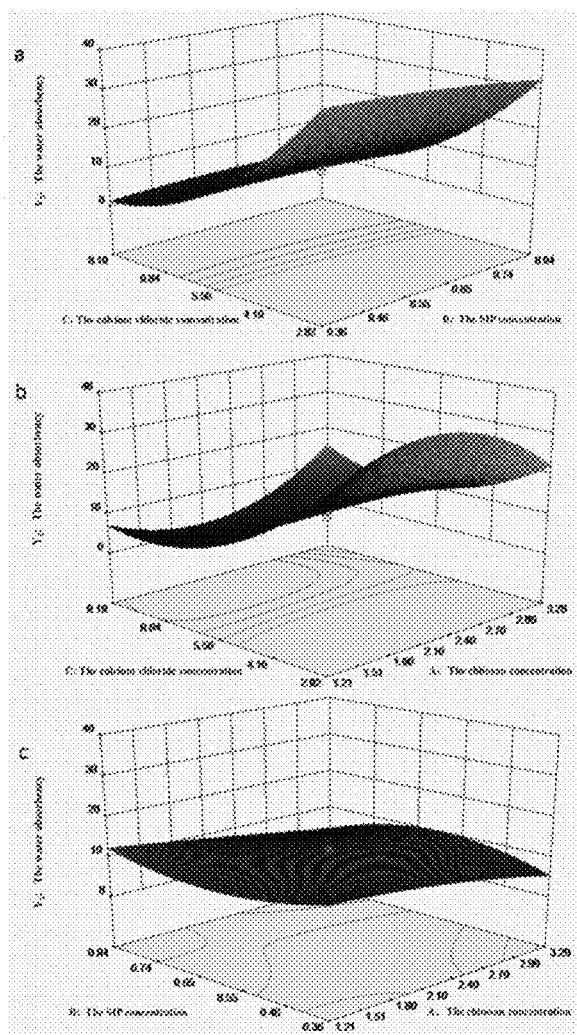
Figure 3:
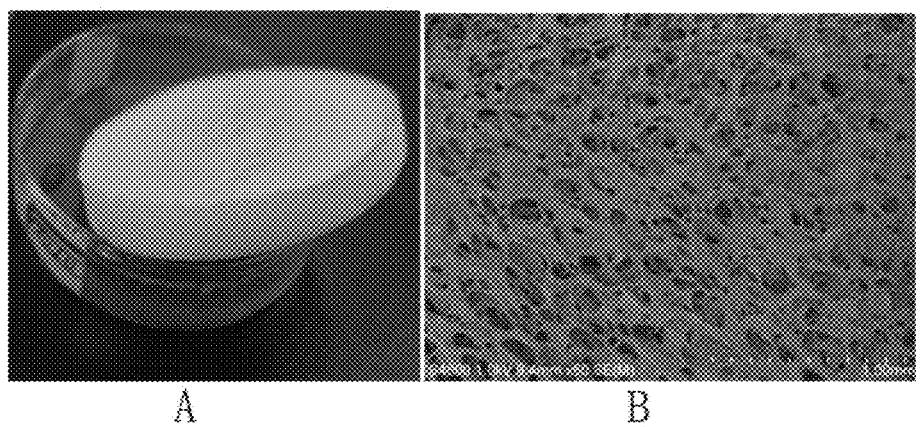
Figure 4:
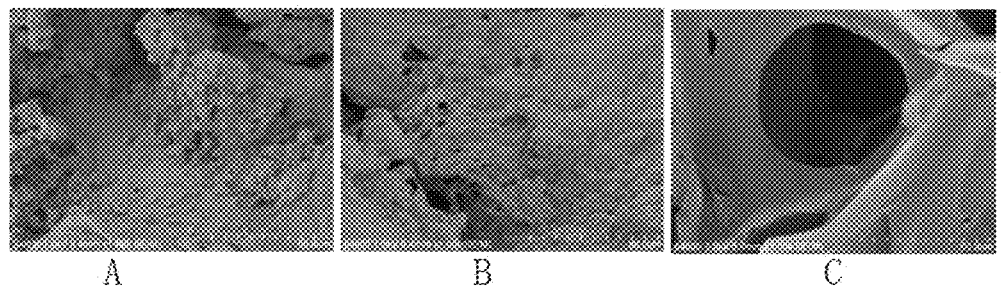
Figure 5:
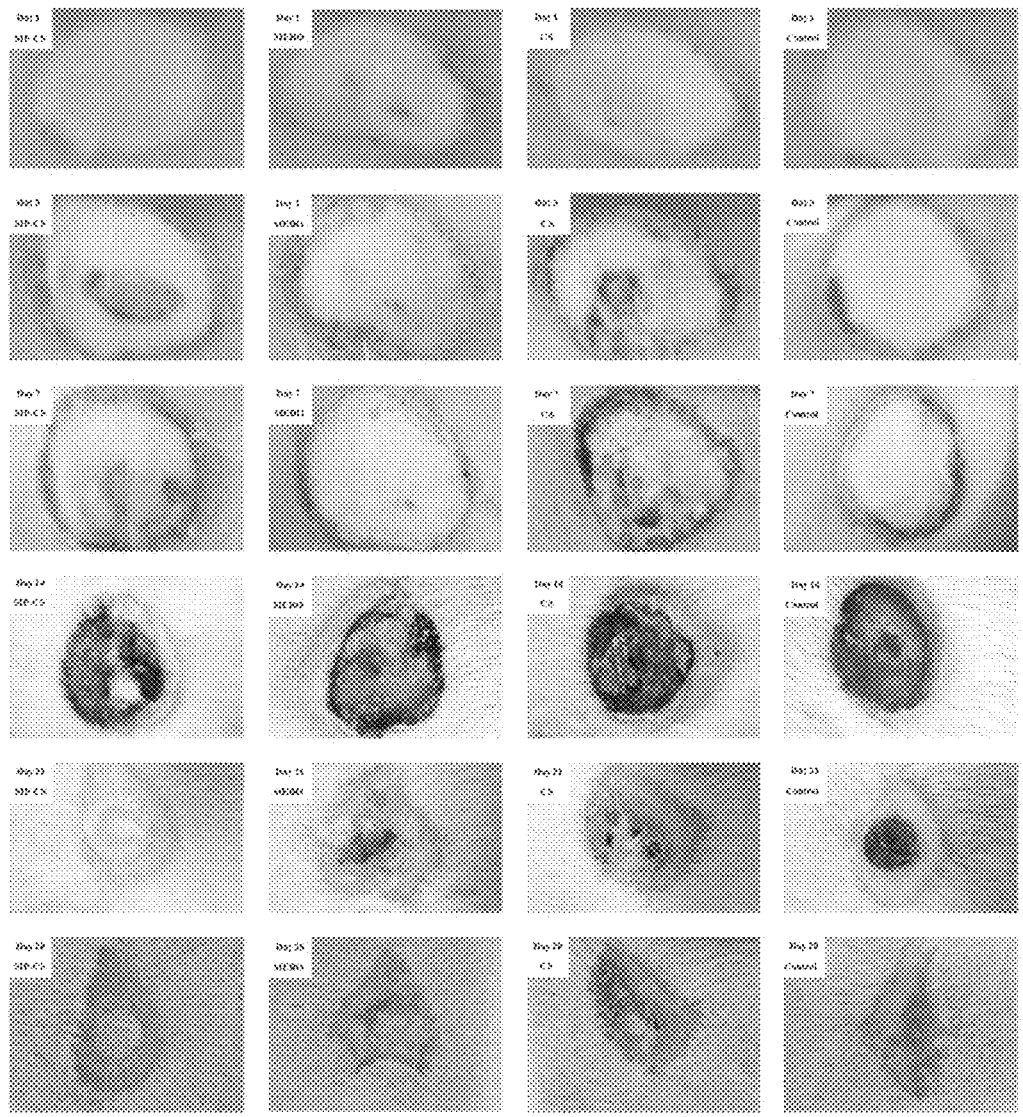

Having thus described the invention in general terms, reference will not be made to the accompanying drawings, which are not necessarily drawn to scale, and wherein:

FIG. 1 shows a response surface of a comprehensive score of appearance quality, and particularly a: response surface according to a SIP concentration and a calcium chloride concentration (a chitosan concentration was fixed at 2.25%); b: response surface according to the chitosan concentration and the calcium chloride concentration (the SIP concentration was fixed at 0.60%); c: response surface according to the chitosan concentration and the SIP concentration (the calcium chloride concentration was fixed at 2.82%);

FIG. 2 shows a response surface of a water absorption capacity, and particularly a: response surface according to the SIP concentration and the calcium chloride concentration (the chitosan concentration was fixed at 2.25%); b: response surface according to the chitosan concentration and the calcium chloride concentration (the SIP concentration was fixed at 0.60%); c: response surface according to the chitosan concentration and the SIP concentration (the calcium chloride concentration was fixed at 2.82%);

FIG. 3 shows an external view of SIP-CS (A) and a SEM image of SIP-CS (B);

FIG. 4 shows the SEM images of three sponges after coagulation, and particularly a: SIP-CS; b: chitosan hemostatic sponge; c: absorbable gelatin sponge;

FIG. 5 shows healing effects of the material on a scalded wound; and

Figure 6:
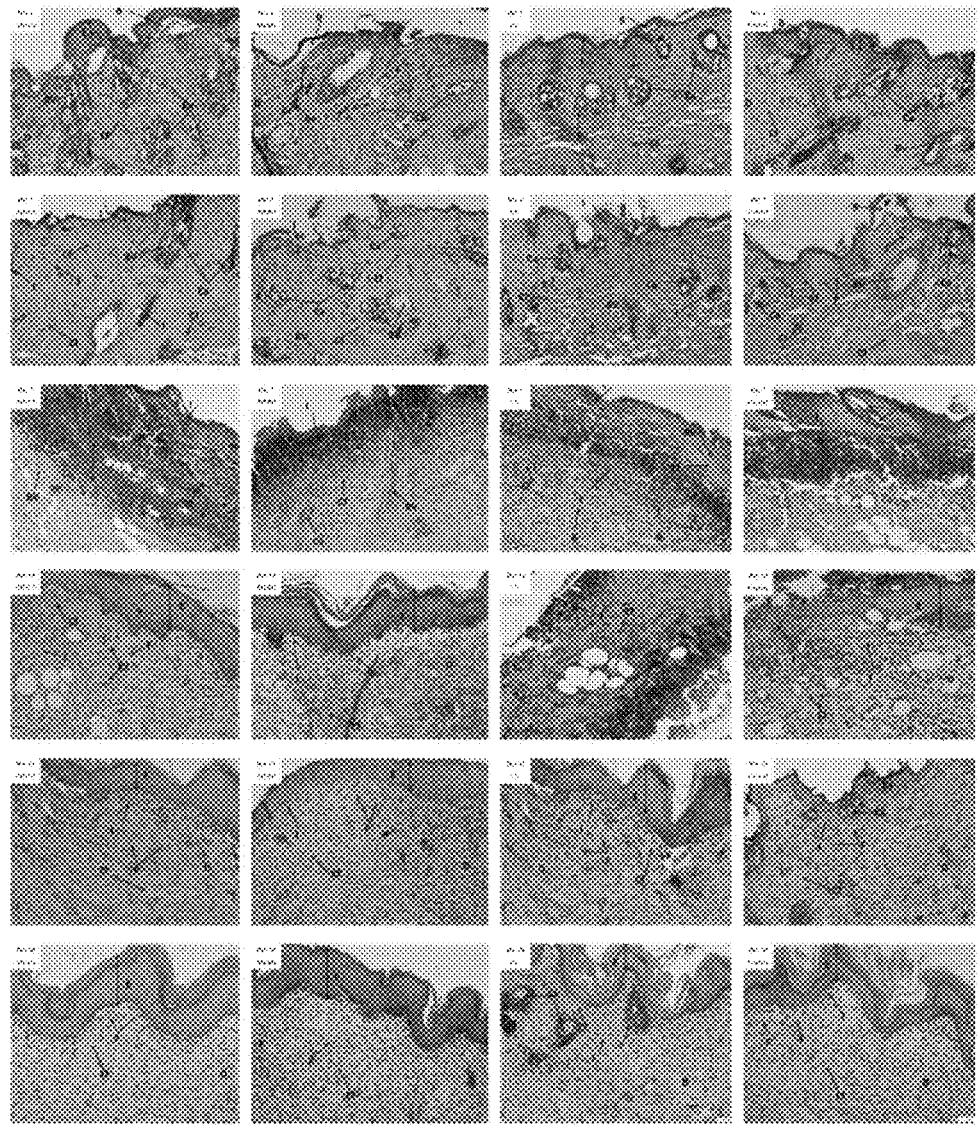

FIG. 6 shows H&E staining of wound tissue sections (×200); noted: B: blister; I: inflammatory cell; BV: blood vessel; Cf: collagen fiber; F: fibroblast; Ca: cutaneous appendage; E: epidermis; D: dermis.

DETAILED DESCRIPTION OF EMBODIMENTS

The present invention will be further described below in combination with accompanied drawings and specific embodiments, but it is not intended to limit the present invention. Without departing from the spirit or essential attributes of the present invention, any modification or replacement to methods, steps and conditions of the present invention shall within the scope of the present invention. Unless specified, experiment methods used in the embodiments are conventional methods and technology to a person skilled in the art, and agents or materials are commercially available.

Materials used in the embodiments below are as follows:
SIP was made in the laboratory (Le X Y et al. Bratislayske Lekarske Listy. 2015).

Chitosan were made in the laboratory (Liu Y et al. J POLYM MATER. 2003) with a deacetylation degree of more than 90%.

GS was purchased from Xiangen Medical Technology Development Co., Ltd (Nanchang, Jiangxi, China).

Medical gauze was purchased from Zhende Medical Co., Ltd (Shaoxing, Zhejiang, China).

Moist exposed burn ointment (abbreviated to "MEBO") was purchased from MEBO Pharmaceuticals Co., Ltd (Shantou, Guangdong, China).

Hematoxylin, eosin Y and neutral balsam were obtained from Shanghai Yuanye Biotechnology Co., Ltd.

Section paraffin was purchased from Hualingkangfu Equipment Co., Ltd (Shanghai, China).

Statistical approach of data in the below embodiments is as follows: the data were processed by IBM SPSS Statistics 22 software and were analyzed using an independent-sample T-test. Numerical data were expressed as mean±SD ($\bar{x}\pm s$). The differences among groups were analyzed by a single factor variance analysis, and if $p<0.05$, it indicates that the difference has statistical significance.

Example 1: Preparation and Evaluation Standard for SIP-CS

1. Preparation for SIP-CS, Comprises Steps as Follows:
(1) dissolving chitosan (CS) in 1% acetic acid solution to obtain a chitosan solution (solution A) and dissolving squid ink polysaccharide (SIP) in purified water to obtain a squid ink polysaccharide solution (solution B).

(2) adding 15 mL of solution A into a 50 mL-beaker and slowly adding 5 mL of solution B thereto with stirring uniformly.

(3) adding 2 mL of calcium chloride solution into the beaker in step (2) with further stirring in speeding up to make a homogenous solution, which was then poured into a culture dish with a diameter of 6 cm until a gel was formed. The gel was observed. When the gel was formed completely, the culture dish was transferred to be frozen at −20° C. for 12 hours, and then lyophilized for another 16 hours to obtain a porous spongy solid, i.e. a wound-healing and hemostatic sponge of squid ink polysaccharide/chitosan (SIP-CS).

2. Evaluation Standard for SIP-CS

The Evaluation standard comprises two parts:

Part One: The Comprehensive Score of Appearance Quality of the Sponge (Y1)

The appearance quality was scored according to gross appearance, surface features and morphology, of the prepared wound-healing and hemostatic sponge with a maximum total score of 50. A specific grading rule is as follows:

(1) Gross Appearance (Maximum Score of 20)

The sponge was scored according to the shape and color with 10 points for each. A smooth circular shape was scored a maximum of 10 points; if the shape was not circular, showing depressions or protrusions, points were deducted from the score accordingly, with a minimum score being 1 point. A uniform and white color was scored 10 points. If the color was yellowish or non-uniform, points were deducted from the score accordingly; more points were deducted for the more yellowish sponge, with the minimum score being 1 point.

(2) Surface Features (Maximum Score of 10)

A surface with a consistent density, spongy shape, light texture, high elasticity and good handle was scored 10 points. Any obvious cracks, uneven pore thickness on the surface and poor elasticity led to a deduction of points accordingly, with the minimum score being 1 point.

(3) Morphology (Maximum Score of 20)

A surface structure of a thin layer was torn off a surface of sponge and observed by a binocular biological microscope. A network structure with uniformly distributed open pores on the surface was scored 20 points. If the network structure was not evident or the pores were not uniformly distributed, points were deducted from the score accordingly, with the minimum score being 1 point.

Part Two: Water Absorption Capacity of the Sponge (Y2)

A piece of sponge (1 cm×1 cm) was cut out, weighed (noted as W1) and then immersed in the purified water of 20° C. After fully absorbing water, the sponge was lifted out of the water by picking up a corner of the sponge with tweezers, and weighed after draining naturally for 30 seconds (noted as W2) with a precision of 0.001 g. The water absorption capacity was calculated as (W2−W1)/W1.

Example 2: Investigation of Influence of the Single Factor on Preparing the SIP-CS The influences of factors, such as molecular weight of chitosan, mass concentration of chitosan, concentration of SIP, solution ratio (solution A to solution B) and mass concentration of calcium chloride, on the preparation for the SIP-CS are firstly investigated, so as to further optimize preparation process.

1. Influence of the Molecular Weight of Chitosan on the Preparation Process for SIP-CS The molecular weight of chitosan was chosen as a single-factor variable, the mass concentration of chitosan was fixed at 2.5%, the concentration of squid ink polysaccharide was fixed at 0.6 mg/ml, a volume ratio of solution A to solution B was fixed at 3:1, and the mass concentration of calcium chloride was fixed at 4%. According to above preparation method, the wound-healing and hemostatic sponge of squid ink polysaccharide/chitosan (SIP-CS) was prepared to investigate the influence of the molecular weight of chitosan on the preparation process for SIP-CS. Experiment result is shown in Table 1.

TABLE 1

Influence of the molecular weight of chitosan on the preparation process for SIP-CS

| molecular weight of chitosan | appearance quality (50 points) | | | | water absorption status | |
| --- | --- | --- | --- | --- | --- | --- |
| | gross appearance (20 points) | surface features (10 points) | microscope figure (20 points) | total score (50 points) | water absorption capacity | remarks |
| 10 thousand | 7 | 5 | 14 | 26 | 30.35 | poor stability in the water and poor adsorbability |
| 200 thousand | 18 | 9 | 15 | 42 | 17.41 | |
| 400 thousand | 18 | 7 | 14 | 39 | 8.62 | |
| 600 thousand | 18 | 8 | 12 | 38 | 10.07 | |
| 800 thousand | 18 | 8 | 14 | 40 | 13.55 | poor stability in the water |

The result shows that the comprehensive score of appearance quality (Y1) of the sponge increased with the molecular weight of chitosan. However, the water absorption capacity reduced. Although the water absorption capacity of the composite wound-healing and hemostatic sponge with the molecular weight of chitosan of ten thousand was the highest, the sponge dissolved easily in the water with poor adsorbability, which was not beneficial for sticking to the wound. Thus, chitosan with a molecular weight of 200 thousand was chosen to prepare the sponge.

2. Influence of the Mass Concentration of Chitosan on the Preparation Process for SIP-CS The mass concentration of chitosan was chosen as the single-factor variable, the molecular weight of chitosan was fixed at 200 thousand, the concentration of squid ink polysaccharide was fixed at 0.6 mg/ml, the volume ratio of solution A to solution B was fixed at 3:1, and the mass concentration of calcium chloride was fixed at 4%. According to above preparation method, the SIP-CS was prepared to investigate the influence of the mass concentration of chitosan on the preparation process for SIP-CS. Experiment result is shown in Table 2.

TABLE 2

Influence of the mass concentration of chitosan on the preparation process for SIP-CS

| mass concentration of chitosan | appearance quality (50 points) | | | | water absorption status | |
| --- | --- | --- | --- | --- | --- | --- |
| | gross appearance (20 points) | surface features (10 points) | microscope figure (20 points) | total score (50 points) | water absorption capacity | remarks |
| 0.5% | 10 | 3 | 7 | 20 | — | dissolved immediately when soaking, unable to be measured |
| 1.5% | 11 | 4 | 17 | 32 | 19.62 | |
| 2.5% | 15 | 8 | 16 | 39 | 25.24 | |
| 3.5% | 17 | 7 | 13 | 37 | 26.99 | |
| 4.5% | 13 | 5 | 16 | 34 | 17.63 | too hard texture |

The result shows that when the mass concentration of chitosan was lower than 0.5%, the product did not form a spongy shape and was easily dissolved in water. Thus, it was impossible to measure the water absorption capacity, while the mass concentration of chitosan was higher than 4.5%, the texture of the composite sponge was hard and the water absorption capacity was also reduced. Thus, the mass concentration of chitosan was chosen as one of the investigation factors.

3. Influence of the Concentration of Squid Ink Polysaccharide on the Preparation Process for SIP-CS The concentration of squid ink polysaccharide was chosen as the single-factor variable, the molecular weight of chitosan was fixed at 200 thousand, the mass concentration of chitosan was fixed at 2.5%, the volume ratio of solution A to solution B was fixed at 3:1, and the mass concentration of calcium chloride was fixed at 4%. According to above preparation method, the SIP-CS was prepared to investigate the influence of the concentration of squid ink polysaccharide on the preparation process for SIP-CS. Experiment result is shown in Table 3.

It is found in the experiment that the concentration of SIP that were too high or too low also affected the appearance quality and water absorption capacity of the sponge. Thus, the concentration of SIP was also included as an investigation factor.

4. Influence of the Volume Ratio of Solution a to Solution B on the Preparation Process for SIP-CS The volume ratio of solution A to solution B was chosen as the single-factor variable, the molecular weight of chitosan was fixed at 200 thousand, the mass concentration of chitosan was fixed at 2.5%, the concentration of squid ink polysaccharide was fixed at 0.6 mg/ml, and the mass concentration of calcium chloride was fixed at 4%. According to above preparation method, the SIP-CS was prepared to investigate the influence of the concentration of squid ink polysaccharide on the preparation process for SIP-CS. Experiment result is shown in Table 4.

TABLE 3

Influence of the concentration of squid ink polysaccharide on the preparation process for SIP-CS

| concentration of squid ink polysaccharide | appearance quality (50 points) | | | | water absorption status | |
| --- | --- | --- | --- | --- | --- | --- |
| | gross appearance (20 points) | surface features (10 points) | microscope figure (20 points) | total score (50 points) | water absorption capacity | remarks |
| 0.2 mg/ml | 11 | 4 | 14 | 29 | — | dissolved immediately when soaking, unable to be measured |
| 0.4 mg/ml | 15 | 8 | 16 | 39 | 30.61 | |
| 0.6 mg/ml | 16 | 7 | 15 | 38 | 20.83 | |
| 0.8 mg/ml | 16 | 6 | 16 | 38 | 17.95 | |
| 1.0 mg/ml | 10 | 5 | 13 | 28 | — | dissolved immediately in the water, unable to be measured |

TABLE 4

Influence of the volume ratio of solution A to solution
B on the preparation process for SIP-CS

| volume ratio (solution A to solution B) | appearance quality (50 points) | | | | water absorption status | |
|---|---|---|---|---|---|---|
| | gross appearance (20 points) | surface features (10 points) | microscope figure (20 points) | total score (50 points) | water absorption capacity | remarks |
| 1:1 | 12 | 4 | 12 | 28 | 17.89 | dissolved easily after soaking |
| 2:1 | 17 | 6 | 15 | 38 | 8.36 | |
| 3:1 | 17 | 8 | 16 | 41 | 10.14 | |
| 4:1 | 17 | 6 | 10 | 33 | 13.51 | dissolved easily after soaking |
| 5:1 | 16 | 7 | 13 | 36 | 7.03 | poor stickiness and poor adsorbability after soaking |

As shown in the result, it is found in the experiment of the volume ratios of solution A to solution B (volume ratio of SIP to CS) that when the ratio was 2:1 and 5:1, the water absorption capacity was low, the stickiness of the sponge was poor, and the sponge was easily dissolved after soaking. Therefore, these ratios were not appropriate for a sponge preparation. When the ratios were 1:1 and 4:1, the resulting sponge had high water absorption capacity, but Y1 was low. Moreover, the stability after soaking was not good and the sponge dissolved easily in the water, which was not conducive to hemostasis. Thus, a ratio (solution A:solution B) of 3:1 was chosen as a fixed level for the sponge preparation.

5. Influence of the Mass Concentration of Calcium Chloride on the Preparation Process for SIP-CS The mass concentration of calcium chloride was chosen as the single-factor variable, the molecular weight of chitosan was fixed at 200 thousand, the mass concentration of chitosan was fixed at 2.5%, the concentration of squid ink polysaccharide was fixed at 0.6 mg/ml, and the volume ratio of solution A to solution B was fixed at 3:1. According to above preparation method, the SIP-CS was prepared to investigate the influence of the mass concentration of calcium chloride on the preparation process for SIP-CS. Experiment result is shown in Table 5.

TABLE 5

Influence of the mass concentration of calcium
chloride on the preparation process for SIP-CS

| mass concentration of calcium chloride | appearance quality (50 points) | | | | water absorption status | |
|---|---|---|---|---|---|---|
| | gross appearance (20 points) | surface features (10 points) | microscope figure (20 points) | total score (50 points) | water absorption capacity | remarks |
| 1% | 17 | 5 | 14 | 36 | 16.96 | too hard texture |
| 2% | 18 | 8 | 17 | 43 | 16.30 | |
| 4% | 17 | 8 | 15 | 40 | 21.99 | |
| 6% | 14 | 7 | 15 | 36 | 9.52 | |
| 10% | 14 | 6 | 15 | 35 | — | dissolved immediately in the water, unable to be measured |

The result shows that the mass concentration of calcium chloride which were too high or too low affected the appearance quality of the sponge. A too-low concentration made the texture too hard to have the same sponginess as the other products, whereas a too-high concentration made the sponge dissolve very fast with an unstable structure. Therefore, the mass concentration of calcium chloride was also included in the central composite design as an optimization factor.

Example 3: Preparation for a CCD-Optimized Sponge

1. The mass concentration of chitosan (Factor A), the concentration of SIP (Factor B), and the mass concentration of calcium chloride (Factor C) were chosen as investigation factors to further optimize the preparation process conditions. A total of 20 combinations including three factors and five levels were generated by the Design-Expert 8.0.6 software, using Y1 and Y2 as evaluation indices (see Table 6).

The comprehensive score of appearance quality (Y1) and the water absorption capacity (Y2) for twenty SIP-CSs are shown in Table 6. Y1 and Y2 were taken as dependent variables. A multiple linear regression, a binomial fitting and a trinomial fitting were performed on each dependent and independent variable. The independent variables were the mass concentration of chitosan (A), the concentration of squid ink polysaccharide (B), and the mass concentration of calcium chloride (C). It was found that the influence of experimental factors on effective values revealed the absence of a simple linear relationship, and multiple correlation coefficients in the following multiple trinomial fitting equations were relatively high:

$$Y1=41.27+3.24A+1.19B-0.74C+0.99AB+1.12AC+1.11BC-3.25A^2-2.11B^2+0.29C^2+0.62ABC-0.20A^2B-0.13A^2C-1.88AB^2(R^2=0.8121, p<0.05);$$

$$Y2=10.53+0.56A-1.18B-16.77C-0.0037AB+3.62AC+1.23BC-0.78A^2-0.88B^2+8.46C^2-0.27ABC+0.52A^2B+9.84A^2C-4.70AB^2(R^2=0.9978, p<0.0001).$$

TABLE 6

Central composite design and result thereof

| order | A/% | B % | C % | Y1 | Y2 |
|---|---|---|---|---|---|
| 1 | 2.25(0) | 0.60(0) | 5.50(0) | 44 | 8.83 |
| 2 | 2.25(0) | 0.60(0) | 5.50(0) | 45 | 9.68 |
| 3 | 3.29(1) | 0.84(1) | 8.18(1) | 41 | 10.1 |
| 4 | 2.25(0) | 0.60(0) | 5.50(0) | 44 | 10.5 |
| 5 | 2.25(0) | 1.00(1.682) | 5.50(0) | 39 | 6.03 |
| 6 | 2.25(0) | 0.60(0) | 5.50(0) | 38 | 11.5 |
| 7 | 2.25(0) | 0.20(−1.682) | 5.50(0) | 35 | 9.99 |
| 8 | 1.21(−1) | 0.84(1) | 2.82(−1) | 35 | 30.0 |
| 9 | 4.00(1.682) | 0.60(0) | 5.50(0) | 40 | 9.25 |
| 10 | 2.25(0) | 0.60(0) | 5.50(0) | 38 | 12.2 |
| 11 | 1.21(−1) | 0.36(−1) | 8.18(1) | 31 | 10.1 |
| 12 | 2.25(0) | 0.60(0) | 1.00(−1.682) | 45 | 62.6 |
| 13 | 3.29(1) | 0.36(−1) | 8.18(1) | 33 | 9.50 |
| 14 | 1.21(−1) | 0.84(1) | 8.18(1) | 32 | 11.9 |
| 15 | 3.29(1) | 0.36(−1) | 2.82(−1) | 36 | 18.1 |
| 16 | 0.50(−1.682) | 0.60(0) | 5.50(0) | 28 | 7.38 |
| 17 | 3.29(1) | 0.84(1) | 2.82(−1) | 37 | 14.8 |
| 18 | 2.25(0) | 0.60(0) | 10.00(−1.682) | 43 | 6.24 |
| 19 | 2.25(0) | 0.60(0) | 5.50(0) | 40 | 10.5 |
| 20 | 1.21(−1) | 0.36 | 2.82(−1) | 36 | 34.3 |

2. Analysis for the Response Surface

According to the trinomial fitting equations, three-dimensional contour line response surfaces of Y1 and Y2 were plotted using the Design-Expert software, wherein one of the three variables was fixed as a mid-value (the results are shown in FIG. 1 and FIG. 2). As shown in FIG. 1, a curved-surface changing degree (c>b>a) indicated that the influence of the mass concentration of chitosan on Y1 was the most significant, followed by the concentration of SIP and the mass concentration of calcium chloride. FIG. 2 shows that the curved-surface changing degree was b>a>c, indicating that the influence of calcium chloride on Y2 was the most significant, followed by the mass concentration of chitosan and the concentration of SIP. Therefore, SIP-CS could not be optimized just by changing the level of one certain factor.

3. Validation of the Optimal Formulation

The largest areas of Y1 and Y2 in FIG. 1 and FIG. 2 were the optimal process ranges of the three independent variables as follows: the mass concentration of chitosan, 2.10%-2.99%; the concentration of SIP, 0.46%-0.74%; and the mass concentration of calcium chloride, 2.82%-4.16%. These ranges were consistent with the predicted optimal values (the mass concentration of chitosan, 2.29%; the concentration of SIP, 0.55%; the mass concentration of calcium chloride, 2.82%). The samples were spongy and porous, with good toughness and a white color, as shown in FIG. 3. Each experiment was conducted in triplicate. An experimental value of the comprehensive score of SIP-CS ($\bar{Y}1=41$) was in good agreement with a predictive value (Y1=42) with a deviation of 2.38%. An experimental value of water absorption capacity ($\bar{Y}2=34.5$) was close to a predictive value (Y2=36.1) with a deviation of 4.43%. This indicates that numerical models established in the present invention can predict these values effectively. Furthermore, the process conditions for preparing the sponge were optimized successfully.

4. Comprehensive Analysis.

In a certain range, the comprehensive score of appearance quality of the sponge and the water absorption capacity of the sponge can be improved when the mass concentration of chitosan and the concentration of squid ink are suitably increased while the mass concentration of calcium chloride is suitably decreased. By the comprehensive evaluation of appearance quality (an average score over 40 points) and the evaluation of water absorption capacity (an average score over 20 points), the optimal formulation of the SIP-CS in the present invention is as follows: the mass concentration of chitosan, 2.29%; the concentration of SIP, 0.55%; the mass concentration of calcium chloride, 2.82%.

Example 4: Animal Hemostasis Experiments

1. Experimental Animals:

one hundred and ten New Zealand rabbits (half male and half female, conventional grade) weighing 1.5-1.8 kg before modeling were provided by Guangdong Medical Laboratory Animal Center, with an experimental animal production license of SCXK(Yue)2014-0035 and an experimental animal quality certificate No. 444116000016. The rabbits were fed in an animal house (conventional grade) of Experimental Animal Center of Guangdong Medical University with an experimental office use license No. SYXK(Yue)2015-0147. The rabbits were individually housed with free access to water and food under the following conditions: 20° C. to 26° C. temperature, 40% to 70% humidity, and 10 hours light/14 hours dark cycles. Drinking water and feeds were provided by Guangdong Medical Laboratory Animal Center. The animals were quarantined for 6 days and checked once daily during the quarantine. No sick animal was found and all the New Zealand rabbits were brought into the experiments. They were anesthetized with 3% pentobarbital sodium (30 mg/kg) via ear vein. Experimental operation was performed in accordance with the ARRIVE guidelines (Kilkenny C, Browne W J, Cuthill I C, Emerson M, Altman D G. Improving bioscience research reporting: the ARRIVE guidelines for reporting animal research. Osteoarthritis Cartilage 2012 2012-04-01; 20(4):256-260).

2. Evaluation of Hemostatic Effect

Thirty New Zealand rabbits were used in an ear artery hemorrhage model and a liver hemorrhage model, and were randomly divided into three groups, i.e. the SIP-CS, CS and GS groups (ten for each group). Twenty New Zealand rabbits were used to establish a femoral artery hemorrhage model, and were randomly divided into the SIP-CS and the CS groups (ten for each group). Materials of the SIP-CS, CS and GS groups were cut into pieces sized 2 cm×2 cm×0.4 cm, weighed on sterile medical gauze (sized 2 cm×2 cm), and recorded an initial weight as m1.

(1) Ear Artery Hemorrhage Model

After anesthesia, the rabbit ears were de-haired and sterilized. A wound sized 1 cm×1 cm was created in the center of the dorsal side of the ear using a surgical knife. The ear artery and vein were cut horizontally without being cut through, so as to prevent the blood from bleeding out of an inner side of the rabbit ear and thus influencing the observation. When the blood from the wound covered a wound surface, a hemostatic material was immediately placed on a bleeding site on the rabbit ear with the sterile medical gauze, followed by manual compression to stop the bleeding. The bleeding was observed every 30 seconds until it stopped, and a hemostatic time was recorded (Ersoy G, Kaynak M F, Yilmaz O, Rodoplu U, Maltepe F, Gokmen N. Hemostatic effects of microporous polysaccharide hemosphere in a rat model with severe femoral artery bleeding. ADV THER 2007 2007-05-01; 24(3):485-492). The sponge and sterile medical gauze were accurately weighed again and their weight was recorded as m2. An absorbed blood volume was calculated as follows: absorbed blood volume (m)=total weight after hemostasis (m2)—total weight before hemostasis (m1). In addition, any secondary re-hemorrhage that occurred within 30 minutes after successful hemostasis in the ear artery was recorded.

The results are shown in Table 7. In the New Zealand rabbit ear artery hemorrhage model, material of the SIP-CS group could stop bleeding rapidly and the hemostatic time was the shortest, so the absorbed blood volume was the smallest, followed by the CS group, and data of the GS group was the worst. In the SIP-CS group, hemostasis was achieved in five rabbits within 1 minute and in five within 1.5 minutes. The hemostatic time was longer in the CS group; hemostasis was achieved in two rabbits within 1 minute, four within 1.5 minutes, two within 2 minutes, and two within 3 minutes. Only two rabbits in the GS group achieved hemostasis within 4 minutes and the remaining eight took longer than 4 minutes. The hemostatic time in the SIP-CS group was shortened by 37.97% and 81.05% compared with the CS and GS groups, respectively. Moreover, the blood volume was decreased by 47.54% and 67.01%, respectively. Additionally, the number of cases with re-hemorrhage in the SIP-CS, CS and GS groups was 0, 3 and 9, respectively.

TABLE 7

Results of SIP-CS for healing three types of wounds in the present invention

| hemorrhage model | group | hemostatic time (min) | | | | | | average hemostatic time (s) | absorbed blood volume (g) |
| --- | --- | --- | --- | --- | --- | --- | --- | --- | --- |
| | | 1 | <1.5 | 2 | 3 | <4 | >4 | | |
| rabbit ear artery | SIP-CS | 5 | 5 | — | — | — | — | 52.58 ± 22.63 | 0.064 ± 0.024 |
| | CSGS | 2 | 4 | 2 | 2 | — | — | 84.77 ± 31.72* | 0.122 ± 0.070* |
| | | — | — | — | — | 2 | 8 | 277.5 ± 80.36** | 0.194 ± 0.068* |
| rabbit liver | SIP-CS | 2 | 6 | 2 | — | — | — | 76.53 ± 21.29 | 0.191 ± 0.086 |
| | CS | — | 4 | 2 | 3 | — | 1 | 120.6 ± 57.17* | 0.400 ± 0.200** |
| | GS | — | — | — | — | 4 | 6 | 241.7 ± 25.99** | 0.794 ± 0.335* |
| rabbit femoral artery | SIP-CS | 1 | 3 | 1 | 3 | 2 | — | 125.7 ± 50.40 | 0.223 ± 0.066 |
| | CS | — | 1 | — | 1 | 4 | 4 | 215.0 ± 85.61* | 0.492 ± 0.375* | noted:
*p < 0.05;
**p < 0.01o (2) Liver Hemorrhage Model

The rabbit ear artery hemorrhage experiment did not have any severe effects on important organs. Thus, after the ear wounds had recovered, 30 rabbits were used to establish the liver hemorrhage model. The rabbits were anesthetized and fixed on an operating table. The abdomen was de-haired, sterilized, and cut layer-by-layer with the surgical knife, keeping the incision as small as possible. When the liver was seen, it was slowly pulled out and the sterile medical gauze was put below the liver to prevent the liver from sliding back to the abdominal cavity. An incision sized 1 cm×1 cm (depth, 0.3 cm) was created in the hepatic lobe using the surgical knife to complete the rabbit liver hemorrhage model. The bleeding was stopped by manual compression as described above, and the hemostatic time and absorbed blood volume were recorded.

The results are shown in Table 7. The data from the rabbit liver hemorrhage model were similar to those from the rabbit ear artery hemorrhage model. The hemostatic effect of the SIP-CS group was the best, followed by the CS group, and the effect of the GS group was the worst. For the hemostatic effect on the rabbit liver, in the SIP-CS group, hemostasis was achieved in two rabbits within 1 minute, six within 1.5 minutes, and two within 2 minutes. In the CS group, four rabbits achieved hemostasis within 1.5 minutes, two within 2 minutes, three within 3 minutes, and one beyond 4 minutes. In the GS group, four achieved hemostasis within 4 minutes and six took longer than 4 minutes. The hemostatic time in the SIP-CS group was shortened by 36.54% and 68.34% compared with the CS and GS groups, respectively. The blood volume was decreased by 52.25% and 75.94%, respectively. Furthermore, no re-hemorrhage occurred within 30 minutes in any group.

(3) Femoral Artery Hemorrhage Model

Because the GS could not successfully stop wound bleeding in the femoral artery within 15 minutes, the GS could not be used to stop massive hemorrhage in the femoral artery. Therefore, the hemostatic effects were only compared between the SIP-CS and CS.

The rabbits in a supine position were anesthetized, de-haired and sterilized on the operating table. One of the thighs was dissected and surrounding tissues were separated to locate the femoral artery. A distal end of the femoral artery was nipped with sterilized hemostatic forceps, and a proximal end of the femoral artery was nipped with sterilized tweezers. Then, a 1 mL syringe with a needle was used to longitudinally puncture the femoral artery. If profuse bleeding occurred in the femoral artery after releasing the tweezers, the model was successful. After a femoral artery wound hemorrhage model was established, the tweezers in the proximal end were released and the distal end was still nipped by the hemostatic forceps. After profuse bleeding occurred in the femoral artery, a sample was immediately used to compress the wound for hemostasis. The material was removed every 30 seconds after 60 seconds of compression to observe the hemostatic effect until hemostasis was achieved in the femoral artery wound. The hemostatic time and bleeding volume were recorded.

The results are shown in Table 7. The experimental result of the rabbit femoral artery model were similar to the above two models. The SIP-CS had the best hemostatic effect among three groups: one achieved hemostasis within 1 minute, three within 1.5 minutes, one within 2 minutes, three within 3 minutes, and two within 4 minutes. In the CS group, one achieved hemostasis within 1.5 minutes, one within 3 minutes, four within 4 minutes, and four beyond 4 minutes. The hemostatic time and absorbed blood volume in the SIP-CS group were shortened by 41.53% and 54.67%, respectively, compared with the CS group. No re-hemorrhage occurred within 30 minutes in either group.

(4) Influence on Blood Cells

Blood was collected from the rabbit ear vein into an anticoagulant tube containing 3.8% sodium citrate (with a volume ratio of blood to sodium citrate of 9:1). The SIP-CS, CS, and GS samples were cut into pieces sized 3×3×3 mm3 respectively, and then 0.5 mL of blood was added to the center of each sample to fully moisten the sponge. After 2 minutes, the sponge was fixed with 2.5% glutaraldehyde for 2 hours, and then any excess blood was washed away with saline. The sponge was then washed with an alcohol gradient (75%, 85%, 95% and 100%) for 15 minutes each, and observed with a scanning electron microscope (SEM, Hitachi S-4800) after being dried and coated with gold (Gu R, Sun W, Zhou H, Wu Z, Meng Z, Zhu X, et al. The performance of a fly-larva shell-derived chitosan sponge as an absorbable surgical hemostatic agent. BIOMATERIALS 2010 2010-02-01; 31(6):1270-1277).

The results showed (as FIG. 4) that there were great differences in the adsorption of blood cells among these three materials, SIP-CS, CS and GS. The SIP-CS possessed good adsorbability, and a great amount of the blood cells were adsorbed in the pores, resulting in an ideal coagulation effect (FIG. 4a). An interaction between the CS and red blood cells were strong, and some of the blood cells were adsorbed (FIG. 4b). As a clinical commonly used hemostatic material, the GS only adsorbed a small amount of the blood cells.

In conclusion, the GS had a poor performance in the evaluation experiment of hemostatic property, especially in the hemorrhage model of artery blood vessel with large bleeding volume. The GS has unsatisfactory hemostatic effect. Although blood clots could be formed, high blood pressure in the artery will easily break through the formed clots, resulting in the re-hemorrhage. This indicates that the GS cannot make the wound surface actively form the blood clot. The wound will be disrupted after manual compression is released, and so the GS cannot be used when emergency therapy is needed. However, the SIP-CS in the present invention performed an excellent performance that it achieved fast hemostasis, and no secondary re-hemorrhage occurred. Because chitosan is sticky, it can improve the hemostatic effect and stop bleeding more easily, as confirmed by observing scanning electron microscope images.

Example 5: Evaluation of Wound Healing in Burnt/Scalded Model

1. Sixty New Zealand rabbits were divided into the control, CS, MEBO, and SIP-CS groups. Each rabbit was evaluated by a self-contrasted method. The rabbits in the control group were only treated with the medical gauze without drug. Rabbits in the other three groups were carried out dressing change every day. Twenty-four hours before the experiment, the rabbits were de-haired by wiping 10% sodium sulfide on a shaving area (sized 10 cm×15 cm) on the back; the skin was then washed with saline. After being anesthetized and sterilized with 75% alcohol in the shaved area on the back, four scalded wound surfaces with an area of 3 cm2 were created 2 cm away from a lateral midline on the rabbit back using a temperature-control scald instrument (YLS-5Q). The scald conditions were as follows: probe temperature, 100° C.; working pressure, 1000 g, contact time between the probe and skin, 5 seconds.

2. Index Measurements (1) Conventional Observation:

wound size, color, inflammation, exudation, infection, incrustation and decrustation were observed on the day of modeling and when the dressing change was done.

(2) Detection of a Wound-Healing Rate:

on days 0, 3, 7, 11, 14, 17, 21, 25 and 28 after the model was created, the scalded wound surface on the rabbit back was covered with a standard translucent weighing paper, and wound edges were drawn on the translucent weighing paper. Then, a wound shape was cut out of the translucent weighing paper and weighed by an electronic analytical balance with precision of one in one hundred thousand. The wound-healing rate was calculated as the follow equation:

wound-healing rate (%)=(weight of paper with an initial wound surface−weight of paper with a healing wound surface)/weight of paper with an initial wound surface×100%.

(3) Observation of Pathological Histology:

on days 1, 3, 7, 14, 21 and 28 after the model was created, ten New Zealand rabbits were randomly selected (five males and five females) to be put to death. Tissues around the wound were cut out and fixed with Bouin's fixative for making pathological sections. Then, the pathological sections were stained with hematoxylin-eosin. Wound-healing status of each group was observed via a fluorescence microscope (Olympus, IX73).

3. Experimental Result (1) Observation of Clinical Status

As shown in FIG. 5, malacia, whitening and edema occurred on the scalded wound surface after modeling. On day 3, symptoms such as necrosis and edema appeared on the scalded wound surface in each group, with tissue fluid effusion. In addition, margin of the wound surface was enlarged, with swelling around the wound. On day 7, the edema on the wound surface in the SIP-CS and MEBO groups began to disappear, leaving the wound surface clean and dry. The wound surfaces in the control and CS groups were wet, without obvious disappearance of the edema. On day 14 after modeling, the incrustation on the wound surface of all groups occurred and the decrustation began from outer edges, leading to smaller wound surface. Shrinkage of the wound surface was better in the SIP-CS group than the control, CS and MEBO groups. On day 21, central parts of the wounds in the control, CS, and MEBO groups had not recovered completely with reddish scabs adhered; the scabs had almost completely fallen off in the SIP-CS group. On day 28, the scabs in all groups had almost completely fallen off, and no hair growth was found in the wound surface area. However, a small amount of hairs were found on the wound surface in the SIP-CS group.

(2) Comparison of the Wound-Healing Rates

As shown in Table 8, the wound healing in the control group took the longest time, and the wound-healing rates were significantly improved in the CS, MEBO and SIP-CS groups compared with that in the control group. Wound-healing effect of the SIP-CS group was equivalent with that of the positive control (the MEBO group), and was even better than the MEBO group during the late stage of therapy (on days 21, 25 and 28 after drug administration).

corneum was rebuilt, and the dermal mesenchyme was dense with fibroblast in an arrangement of spindle-shaped uniform layer. On day 21, the wound re-epithelialization was obvious in the CS group, while most of the wound re-epithelialization in the MEBO group had completed, and the wound re-epithelialization in the SIP-CS group had already finished. On day 28, the wound re-epithelialization was completed in the control, CS, MEBO and SIP-CS groups. In the SIP-CS group, thickening of the epidermis was the most significant, and the dermal mesenchyme was dense with fibroblast in the arrangement of spindle-shaped uniform layer, indicating the best recovery.

In conclusion, in the evaluation experiment of promoting wound healing, the New Zealand rabbits were chosen to establish the scalded model. Scald, an extremely complicated traumatic disease which is common in the clinic, caused by thermal factor, chemical substances, electric current and radioactive rays, was used to investigate the effect of the sponge on promoting wound healing. Clinical observation of wound recovery indicated that SIP-CS had a significant effect on promoting wound healing in the scald, especially regarding secondary edema and infection during the wound recovery. The spongy dressing was more vapor-permeable than the burn cream commonly used in the clinic. Furthermore, it could be observed from the pathological sections that the SIP-CS could promote epithelial cell neo-

TABLE 8

Wound-healing rates of the control, CS, MEBO and SIP-CS groups (%, n = 10, x ± s)

| measurement time | SIP-CS group | MEBO group | CS group | control group |
|---|---|---|---|---|
| 3 d | 0.56 ± 4.67* | −2.26 ± 6.23 | −3.63 ± 3.77 | −5.31 ± 3.94 |
| 7 d | 12.77 ± 8.00* | 8.62 ± 17.51 | 10.11 ± 8.80* | 3.93 ± 5.76 |
| 11 d | 27.55 ± 6.08 | 25.77 ± 14.50 | 26.95 ± 9.57 | 22.97 ± 6.33 |
| 14 d | 39.44 ± 3.52* | 35.87 ± 8.54 | 34.72 ± 7.29* | 28.82 ± 7.54 |
| 17 d | 41.29 ± 7.36* | 36.35 ± 6.59 | 35.39 ± 7.16* | 30.97 ± 7.00 |
| 21 d | 55.06 ± 6.64*# | 54.71 ± 6.99* | 46.26 ± 5.74 | 40.87 ± 7.23 |
| 25 d | 63.38 ± 9.37*# | 57.25 ± 6.44* | 48.76 ± 12.16 | 47.23 ± 9.55 |
| 28 d | 69.05 ± 6.12**# | 61.34 ± 9.98* | 61.28 ± 8.02* | 48.81 ± 12.24 | compared with the control group:
*$p < 0.05$;
**$p < 0.01$;
compared with the MEBO group:
$p < 0.05$;
$p < 0.01$ (3) Observation of Pathological Histology As shown in FIG. 6, on day 1 after the rabbits were scalded, it was observed that epidermis of the rabbit was severely damaged, showing blisters in dermis and inflammatory cell infiltration. Dermal mesenchyme became loose, and cutaneous appendages such as hair follicles and sweat glands were damaged. The remaining hair follicles and skin appendages could be observed deep in the dermis, consistent with pathological features of a deep second-degree scald. Thus, the burnt/scalded model was established successfully. On day 3 after being scalded, the epidermis in the control group was damaged showing blisters in the dermis, and the mesenchyme was loose. The epidermis was damaged with the cutaneous appendages such as the remaining hair follicles and sweat glands being seen in the dermis in the CS, MEBO and SIP-CS groups. On day 7, obvious scabs and the inflammatory cell infiltration could be seen in each group. On day 14, more inflammatory cells were observed in the SIP-CS and CS groups, and the epidermis had not recovered significantly. Obvious wound re-epithelialization occurred, and the epidermis had recovered well. In addition, stratum genesis, re-epithelialization and repair of the epidermis and dermis. The effect of the SIP-CS on promoting would healing was better than those of the control materials, the CS and MEBO.

Many modifications and other embodiments of the inventions set forth herein will come to mind to one skilled in the art to which the inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A preparation method for a wound-healing and hemostatic sponge of squid ink polysaccharide/chitosan, comprising steps of:

preparing a squid ink polysaccharide and a chitosan as carriers and an initiator for blood coagulation, wherein the initiator for blood coagulation is a calcium chloride solution;

dissolving the squid ink polysaccharide in a first solvent to obtain a squid ink polysaccharide solution, and dissolving the chitosan in a second solvent to obtain a chitosan solution;

mixing and combining the squid ink polysaccharide solution, the chitosan solution, and the calcium chloride solution;

and applying a lyophilization technology to obtain the wound-healing and hemostatic sponge of squid ink polysaccharide/chitosan, wherein the squid ink polysaccharide solution has a concentration of 0.4 to 0.8 mg/mL.

2. The preparation method according to claim 1, wherein the steps comprising slowly adding the squid ink polysaccharide solution to the chitosan solution, to form a uniformly mixed solution, adding the calcium chloride solution to the uniformly mixed solution, to obtain a homogenous solution, forming a gel from the homogenous solution, freezing the gel, and applying the lyophilization technology to lyophilize the gel to obtain the wound-healing and hemostatic sponge of squid ink polysaccharide/chitosan.

3. The preparation method according to claim 1, wherein the chitosan solution has a mass concentration of 1.5 to 3.5%, and the calcium chloride solution has a mass concentration of 2 to 6%.

4. The preparation method according to claim 1, wherein a volume ratio of the squid ink polysaccharide solution, the chitosan solution and the calcium chloride solution is 4-6:13-17:1-3.

5. The preparation method according to claim 1, wherein the squid ink polysaccharide solution has a concentration of 0.55 mg/mL, the chitosan solution has a mass concentration of 2.29%, the calcium chloride solution has a mass concentration of 2.82%, and a volume ratio of the squid ink polysaccharide solution, the chitosan solution and the calcium chloride solution is 5:15:2.

6. The preparation method according to claim 2, wherein a condition for the step of freezing the gel is frozen at −30° C. to −10° C. for 10 to 15 hours.

7. A wound-healing and hemostatic sponge of squid ink polysaccharide/chitosan achieved by the preparation method according to claim 1.

8. A method for hemostasis and/or wound healing, comprising applying the wound-healing and hemostatic sponge of squid ink polysaccharide/chitosan according to claim 7 onto a wound, compressing the wound until hemostasis is achieved, dressing the wound, and replacing the wound-healing and hemostatic sponge of squid ink polysaccharide/chitosan regularly.

9. A wound-healing and hemostatic sponge of squid ink polysaccharide/chitosan, obtained by the preparation method according to claim 2.

10. A wound-healing and hemostatic sponge of squid ink polysaccharide/chitosan, obtained by the preparation method according to claim 3.

11. A wound-healing and hemostatic sponge of squid ink polysaccharide/chitosan, obtained by the preparation method according to claim 4.

12. A wound-healing and hemostatic sponge of squid ink polysaccharide/chitosan, obtained by the preparation method according to claim 5.

13. A wound-healing and hemostatic sponge of squid ink polysaccharide/chitosan, obtained by the preparation method according to claim 6.

14. A method for hemostasis and/or wound healing, comprising applying the wound-healing and hemostatic sponge of squid ink polysaccharide/chitosan according to claim 9 onto a wound, compressing the wound until hemostasis is achieved, dressing the wound, and replacing the wound-healing and hemostatic sponge of squid ink polysaccharide/chitosan regularly.

15. A method for hemostasis and/or wound healing, comprising applying the wound-healing and hemostatic sponge of squid ink polysaccharide/chitosan according to claim 10 onto a wound, compressing the wound until hemostasis is achieved, dressing the wound, and replacing the wound-healing and hemostatic sponge of squid ink polysaccharide/chitosan regularly.

16. A method for hemostasis and/or wound healing, comprising applying the wound-healing and hemostatic sponge of squid ink polysaccharide/chitosan according to claim 11 onto a wound, compressing the wound until hemostasis is achieved, dressing the wound, and replacing the wound-healing and hemostatic sponge of squid ink polysaccharide/chitosan regularly.

17. A method for hemostasis and/or wound healing, comprising applying the wound-healing and hemostatic sponge of squid ink polysaccharide/chitosan according to claim 12 onto a wound, compressing the wound until hemostasis is achieved, dressing the wound, and replacing the wound-healing and hemostatic sponge of squid ink polysaccharide/chitosan regularly.

18. A method for hemostasis and/or wound healing, comprising applying the wound-healing and hemostatic sponge of squid ink polysaccharide/chitosan according to claim 13 onto a wound, compressing the wound until hemostasis is achieved, dressing the wound, and replacing the wound-healing and hemostatic sponge of squid ink polysaccharide/chitosan regularly.

* * * * *